United States Patent

Merianos et al.

[11] Patent Number: 5,008,038
[45] Date of Patent: Apr. 16, 1991

[54] SOLUBILIZATION OF LACTAM AND CHLORHEXIDINE IN WATER

[75] Inventors: John J. Merianos, Middletown; Robert B. Login, Oakland, both of N.J.

[73] Assignee: GAF Chemicals Corporation, Wayne, N.J.

[21] Appl. No.: 419,176

[22] Filed: Oct. 10, 1989

[51] Int. Cl.⁵ .................. B01F 3/20; A61K 31/155
[52] U.S. Cl. ............................. 252/363.5; 514/635
[58] Field of Search ...................... 252/363.5; 514/635

[56] References Cited

U.S. PATENT DOCUMENTS

| | | | |
|---|---|---|---|
| 4,137,332 | 1/1979 | Brown et al. | 514/635 |
| 4,584,192 | 4/1986 | Dell et al. | 514/635 X |
| 4,920,145 | 4/1990 | Cho et al. | 514/635 X |

Primary Examiner—Richard D. Lovering
Assistant Examiner—Gary L. Geist
Attorney, Agent, or Firm—Marilyn J. Maue; Joshua J. Ward

[57] ABSTRACT

Solubility of chlorhexidine free base and hydrocarbon substituted lactams in water is substantially enhanced by forming an aqueous solution of a complex of chlorhexidine free base and lactam. This is preferably done by dissolving chlorhexidine free base in lactam and then mixing the resulting solution with water. The resulting aqueous solution contains between about 1 and about 25 wt % of a complex of lactam and chlorhexidine with chlorhexidine being present in amounts between about 0.08 and about 0.25 wt % based on lactam. Lactam used is defined by the formula

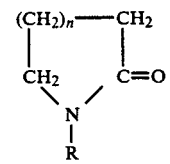

wherein n is an integer having a value of from 1 to 3 and R is a linear alkyl radical containing from 10 to 14 carbon atoms.

10 Claims, No Drawings

SOLUBILIZATION OF LACTAM AND CHLORHEXIDINE IN WATER

THE BACKGROUND OF THE INVENTION

N-lower alkyl pyrrolidones have found wide commercial acceptance as non-toxic aprotic chemical solvents. N-lower alkyl pyrrolidones do not however possess significant aqueous surfactant properties. Long chain alkyl pyrrolidones such as N-dodecyl pyrrolidone are known to be surfactants with good foaming properties. N-dodecyl pyrrolidone is used for instance in the manufacture of toiletries and cosmetics. Use of such long chain alkyl pyrrolidones is however restricted due to their lack of solubility in water N-dodecyl pyrrolidone for instance is soluble in water only to the extent of about 0.1 wt. % to about 0.2 wt. %. The usual method of incorporating long chain alkyl pyrrolidones such as N-dodecyl pyrrolidone in aqueous media is to dissolve the pyrrolidone in a small volume of a water soluble organic solvent such as ethanol and then add this solution to the aqueous medium. This technique has shortcomings. The water insoluble pyrrolidone is very likely to separate out of the aqueous medium. Even if this does not happen, a quantity of organic solvent, sometimes unwanted, is necessarily introduced into the aqueous system.

Another material which is well known but is generally considered insoluble in water is chlorhexidine free base which is soluble in water only to the extent of about 0.008%–0.01% at 25° C. Chlorhexidine digluconate is widely used for instance as a germicide at pH 5.5. At higher pH 8.0 the free base will precipitate out of water. Its use is frequently limited because of its limited solubility in water. It is accordingly an object of the present invention to provide aqueous solutions containing effective amounts of chlorhexidine free base and long chain alkyl lactams. Another object of the invention is to provide a method for preparing such aqueous solutions of chlorhexidine and long chain alkyl lactams.

SUMMARY OF THE INVENTION According to the present invention, a composition of matter is provided which comprises an aqueous solution containing between about 1 and about 25 wt % based on water of a complex of:

a) a long chain alkyl lactam having the formula

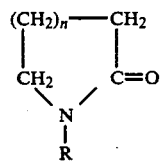

wherein n is an integer having a value of from 1 to 3 and R is a linear alkyl radical containing from 10 to 14 carbon atoms; and b) between about 0.08 wt. % and about 0.25 wt % of chlorhexidine free base based on the lactam present.

According to the invention, there is also provided a method for preparing the aqueous solutions of the invention by first dissolving the chlorhexidine free base in lactam and then mixing the resulting solution of lactam and chlorhexidine complex with water.

DETAILED DESCRIPTION OF THE INVENTION

As mentioned above, the composition of the invention is an aqueous solution of between about 1 and about 25 wt % based on water of a complex of alkyl lactam and between about 0.08 and about 0.25 wt % chlorhexidine free base based on the alkyl lactam. In preferred embodiments, the alkyl lactam is of the formula given above wherein n is an integer having a value of I. An especially preferred embodiment uses N-dodecyl pyrrolidone as the lactam which is complexed with chlorhexidine free base [1,6-bis(p-chlorophenylbiguanido)hexane]. Especially preferred embodiments involve solutions of between about 0.1% and about 0.3 wt % of the lactam-chlorhexidine complex based on water and wherein the complex contains between about 0.08 and about 0.25 wt % chlorhexidine.

The method of the invention broadly contemplates formation of compositions of the invention as defined above by first forming a solution of chlorhexidine free base in the lactam and then adding water to form the composition of the invention. This is preferably done by first heating the lactam to an elevated temperature between about 40° C. and about 60° C. and then adding the chlorhexidine free base to the heated lactam so that the chlorhexidine free base dissolves in the lactam. During the mixing of the chlorhexidine free base with the lactam, the lactam is preferably maintained at a temperature between about 50° and about 60° C. It is also within the scope of the invention to mix the lactam with the chlorhexidine at lower temperatures such as room temperature and then heat the resulting mixture to complete dissolution of chlorhexidine in lactam.

While varying proportions of lactam and chlorhexidine free base may be used, it is preferred that a solution of chlorhexidine free base in lactam contain between about 3 and about 15 wt. % chlorhexidine based on the total of lactam and chlorhexidine free base used. Use of less than about 3 wt. % chlorhexidine free base in the solution with the lactam does not usually result in a significant increase of the water solubility of either the chlorhexidine or the lactam. Use of more than about 15 wt. % of chlorhexidine free base requires excessive temperatures to insure complete dissolution in the lactam.

When chlorhexidine free base has been dissolved in lactam, preferably in a heated solution as mentioned above, the solution is then mixed with water to form the desired aqueous solution containing both chlorhexidine free base and lactam. It is believed that the chlorhexidine free base and lactam are in the form of a complex and that it is this complex which is dissolved in the water.

The non-aqueous solution of lactam and chlorhexidine free base may be mixed with water at elevated temperatures but it is generally preferred to allow the non-aqueous solution to cool to approximately room temperature, e.g. between 70° F and about 80° F, before mixing with the water. If the mixing occurs at elevated temperature the resulting room temperature aqueous solution may then be allowed to cool to room temperature. In either event, the resulting aqueous solution usually contains small amounts of precipitate which may be separated from the solution, e.g. by being allowed to settle or being filtered out so that the resulting aqueous solution is clear and therefore more suitable for most commercial uses. The clear aqueous solution may have some color, but this is not considered a disadvantage for at least most intended uses.

Aqueous solution of the invention may be used in a great variety of applications in which the use of either the lactam or the chlorhexidine alone would normally be considered desirable. These may include for instance, uses in germicidal and sterilizing solutions in which chlorhexidine is normally used as well as use in various personal care products in which the use of lactam solvents would normally be considered, such as use as preservatives in cosmetics and toiletries. Compositions of the present invention have the advantage that aqueous solutions contain significant quantities of both the chlorhexidine and lactam components and may be made and used without the necessity of the other organic solvents which have in the past been needed for use with these components. By use of the present invention, it is possible to obtain room temperature aqueous solutions in which the lactam is present in water in amounts as great as 200 times the maximum amount normally considered soluble in water. Likewise, the chlorhexidine may be present in amounts of as much as 20 times the maximum amount of chlorhexidine normally considered soluble in water.

The following examples illustrate preferred embodiments of the invention, but are not intended to limit the scope of the invention.

In preferred embodiments, compositions of the invention contain at lease 200 times the maximum amount of lactam normally considered soluble in water and at least about 20 times the maximum amount of chlorhexidine normally considered soluble in water.

EXAMPLE 1

An aqueous solution of the invention was prepared by the method of the invention using following ingredients:

| Ingredient | Amount |
|---|---|
| N-dodecyl pyrrolidone | 90 grams |
| chlorhexidine free base | 10 grams |
| water | 400 milliliters |

The chlorhexidine free base was added to the N-dodecyl pyrrolidone and the mixture was warmed to 45° C. with stirring until solution of the chlorhexidine base in the pyrrolidone was completed. The clear solution was then allowed to cool to room temperature. 200 grams of distilled water was then added with constant stirring, which resulted in a very viscous solution in which was dispersed white particulate material. An additional 200 grams of water was added and, after stirring, the resulting solution was allowed to sit overnight. The next morning he resulting room temperature product contained a supernatant, light tan colored liquid and a white precipitate. After filtration to remove the precipitate, the aqueous solution was found to weigh 475 grams and comprised 18.5 wt. % N-dodecyl pyrrolidone, 0.085 wt. % chlorhexidine base, and 81.5 wt. % water. The pH of the solution was 10.9. The white residue weighed 28 grams. The residue was washed with acetone and dried in a vacuum. The dried material weighed 13.5 grams of which 51.35% was N-dodecyl pyrrolidone and 48.55% chlorhexidine base. The remaining 0.25 wt. % was water. Based on a molecular weight of 253 for the N-dodecyl pyrrolidone and 505 for the chlorhexidine base, the dry residue was found to be N-dodecyl pyrrolidone and chlorhexidine base in a molar ratio of 2 to 1.

EXAMPLE 2

5 Grams of chlorhexidine base was dissolved in 95 grams of N-dodecyl pyrrolidone maintained in a water bath at 40° C. The resulting solution was clear and light tan in color. 10 Grams of this solution was then cooled to room temperature and mixed thoroughly with 490 grams of distilled water. Only a small quantity of solids precipitated. By ultraviolet absorption analysis, the filtrate contained 0.0997 wt. % chlorhexidine (theory 0.1 %), 1.60 wt. % N-dodecyl pyrrolidone (theory 1.9 %) and 98.16 % water (theory 98.0%).

EXAMPLE 3

To illustrate the necessity of using an alkyl lactam having at least 10 carbon atoms in the alkyl chain, an attempt was made to practice the invention using N-octylpyrrolidone. In this experiment, 5 grams of chlorhexidine free base dissolved in 95 grams of N-octylpyrrolidone at 40° C. The resulting clear solution was allowed to stand at room temperature and remained clear. A 10 gram aliquot sample was mixed with 490 grams of water to give a two layer product. The top layer was 9.2 grams of N-octylpyrrolidine and the bottom layer was water. The chlorhexidine free base was precipitated out in the interface of the above layers.

From the above examples and description it can be seen that aqueous solutions containing alkyl lactam and chlorhexidine base made in accordance with the invention provide new and highly desirable products which can be used without the presence of organic solvents and which contain far greater amounts of chlorhexidine and lactam than are possible using aqueous solutions of chlorhexidine or lactam alone. Such products can, for instance, be used to formulate antimicrobial liquid soap, which will be stable at alkaline pH 8-8.5.

What is claimed is:

1. A composition of matter comprising an aqueous solution containing between about 1 and about 25 wt. % based on water of a complex of:

(a) an N-hydrocarbon substituted lactam defined by the formula

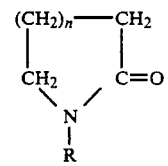

wherein n is an integer having a value of from 1 to 3 and R is a linear alkyl radical containing from 10 to 14 carbon atoms; and (b) between about 0.08 and about 0.25 wt. % chlorhexidine based on lactam.

2. A composition according to claim 1 wherein n is an integer having a value of 1.

3. A composition according to claim 2 wherein the lactam is N-dodecyl pyrrolidone.

4. A composition according to claim 2 wherein the lactam and chlorhexidine are present in a total amount of between about 0.1 and about 0.3 wt. based on water.

5. Method of making the composition of claim 1 which comprises:

(a) dissolving chlorhexidine free base in lactam in an amount between about 3 and about 15 wt. % chlorhexidine free base based on lactam; and
(b) then mixing the solution of chlorhexidine free base in lactam with water to form an aqueous solution containing between about 1 and about 25 wt. % of the solution of lactam and chlorhexidine.

6. Method according to claim 5 wherein n is an integer having a value of 1.

7. Method according to claim 6 wherein the lactam and chlorhexidine free base are heated to an elevated temperature within the range of between about 40° and 60° C. to complete dissolution of the chlorhexidine free base in the lactam before mixing with water.

8. Method according to claim 7 wherein the lactam is N-dodecyl pyrrolidone.

9. Method according to claim 7 wherein the addition of the water to the non-aqueous solution of alkyl pyrrolidone and chlorhexidine results in formation of a precipitate at room temperature and the precipitate is then removed.

10. Method according to claim 9 wherein the precipitate is removed by filtration.

* * * * *